United States Patent [19]
Shepherd et al.

[11] Patent Number: 5,815,547
[45] Date of Patent: *Sep. 29, 1998

[54] RADIATION THERAPY AND RADIATION SURGERY TREATMENT SYSTEM AND METHODS OF USE OF SAME

[76] Inventors: Joseph S. Shepherd, 2004 Le Droit Dr., South Pasadena, Calif. 91030; Robert W. Rand, 521 N. Bristol Ave., Los Angeles, Calif. 90049

[*] Notice: The term of this patent shall not extend beyond the expiration date of Pat. No. 5,748,700.

[21] Appl. No.: 574,155

[22] Filed: Dec. 18, 1995

Related U.S. Application Data

[62] Division of Ser. No. 240,374, May 10, 1994, Pat. No. 5,537,452.

[51] Int. Cl.$^6$ ........................................... A61N 5/10
[52] U.S. Cl. .................................. 378/65; 378/68
[58] Field of Search .................. 378/20, 64, 65, 378/68, 69, 195, 208, 209, 148

[56] References Cited

U.S. PATENT DOCUMENTS

| | | | |
|---|---|---|---|
| 2,139,966 | 12/1938 | Loebell | 378/65 |
| 4,118,631 | 10/1978 | Froggatt | 250/492 R |
| 4,200,799 | 4/1980 | Saito | 250/445 T |
| 4,266,139 | 5/1981 | Sportelli et al. | 250/515 |
| 4,365,341 | 12/1982 | Lam | 378/65 |
| 4,598,415 | 7/1986 | Luccio et al. | 378/119 |
| 4,766,603 | 8/1988 | Okabe et al. | 378/152 |
| 4,780,898 | 10/1988 | Sundqvist | 378/65 |
| 4,988,268 | 1/1991 | Kurihara | 417/312 |
| 4,998,268 | 3/1991 | Winter | 378/63 |
| 5,039,867 | 8/1991 | Nishihara et al. | 378/65 X |
| 5,116,344 | 5/1992 | Sundqvist | 606/130 |
| 5,207,223 | 5/1993 | Adler | 128/653.1 |
| 5,267,294 | 11/1993 | Kuroda et al. | 378/65 |
| 5,329,567 | 7/1994 | Ikebe | 378/65 X |
| 5,537,452 | 7/1996 | Shepherd et al. | 378/65 |

FOREIGN PATENT DOCUMENTS

| | | |
|---|---|---|
| 0 431 785 A1 | 6/1991 | European Pat. Off. . |
| 0 655 262 A1 | 5/1995 | European Pat. Off. . |
| WO 88/05321 | 7/1988 | WIPO . |

OTHER PUBLICATIONS

Confidentiality Agreement, signed by J.Shepherd (Jan. 4, 1993) and D.Blayney (Jan. 5, 1993).

Letter, dated Jan. 23, 1993, to J.Shepherd, from D.Blayney.

Proposal, *The Cobalt Scalpel*, dated Jan. 27, 1993, presented by Nova Therapeutic Systems, Inc.

Healthcare Product Comparison System, "Linear Accelerators; Radiotherapy Units, Cobalt", Oct. 1993, ECRI a nonprofit agency, Plymouth Meeting, PA.

Varian Associates, "Varian Clinac® 600SR", Nov. 1992 (as indicated on last page of the document; Date of public availavility is not known).

Advanced Medical Systems, Inc., "Radsim Simulator—Product Data", Geneva, OH (date not indicated).

(List continued on next page.)

*Primary Examiner*—David P. Porta
*Attorney, Agent, or Firm*—Lyon & Lyon, LLP

[57] ABSTRACT

A radiosurgery and radiotherapy system to provide diagnostic imaging and target localization via a patient 3-D mapping means such as a CT scanner or MRI, patient positioning via a four degree of freedom of motion table, and a stereotactic Cobalt 60 therapy unit incorporating multiple sources to therapeutically irradiate a target is provided. Methods of radiosurgery and radiotherapy utilizing the system are also provided. A combination of radiation source configuration, 360 degree rotational characteristics of the therapy unit, and table movement will allow any size and shape of target to be irradiated to therapeutic levels while decreasing radiation exposure to surrounding healthy tissue. A radiation beam catcher which captures greater than 80% and preferably greater than 90 percent of the radiation from the radiation sources is also provided.

12 Claims, 6 Drawing Sheets

OTHER PUBLICATIONS

Advanced Medical Systems, Inc. "'New' RAD–8—Product Data", Geneva, OH (date not indicated).

Nova Therapeutic Systems, Inc., "$^{60}$ Cobalt Sources—Product Data", Geneva, OH (date not indicated).

Advanced Medical Systems, Inc., "Get Faster Patient Setup with the Unique ATC C/9 $^{60}$ Cobalt Unit", Nova Therapeutic Systems, Inc., South Pasadena, CA (date not indicated.

Nova Therapeutic Systems, Inc., "Five Year Inspection and Preventive Maintenance Program", South Pasadena, CA (date not indicated).

George Anders, The Wall Street Journal, vol. CXXX No. 77, Western Edition, "High–Tech Health; Hospitals Rush to Buy a $3 Million Device Few Patients Can Use; Surgeons Want Gamma Knife for Certain Brian Cases and Often Get Their Way; Two Machines 10 Miles Apart", Apr. 20, 1994.

RADIATION THERAPY AND RADIATION SURGERY TREATMENT SYSTEM AND METHODS OF USE OF SAME

This is a Divisional application of Ser. No. 08/240,374 now U.S. Pat. No. 5,537,452, filed May 10, 1994. This application declares its priority from the parent application which is also incorporated by reference.

BACKGROUND OF THE INVENTION

This invention relates in general to an apparatus and methods for controlling the administration of radiation to a patient, and more particularly, to stereotactically directed radiation apparatus and radiation therapy and surgery performed by the apparatus.

The use of a computerized tomographic (CT) scanner or a Magnetic Resonance Imaging (MRI) system has been generally used to aid in diagnostic procedures or to aid in planning placement of a patient prior to the patient receiving radiation. The patient was then removed from the CT or MRI unit and radiation therapy was performed on a secondary system physically removed from the scanning facility. The employment of a second apparatus was due to the fact that the radiation levels necessary for radiation therapy were incompatible with the levels required for diagnostic procedures. The secondary radiation (scatter) from the treatment system required that it be placed in a separate, shielded room. Attempting to successfully reposition the patient in the secondary device, along with potential physiological changes which may occur in the patient, can cause considerable problems in insuring a successful outcome with minimal danger to the patient.

Radiation therapy has generally been practiced utilizing either a Cobalt 60 radioactive source (1.2 MeV energy) or a linear accelerator with electron energies ranging typically from 4.0 to 20 MeV. Most existing radiation therapy technology provides radiation from a single focal point. Custom shielding blocks, and beam shapers are necessarily utilized in most treatments to deliver a uniform dose to the target without overdosing the surrounding area of healthy tissue. The radiation field size which is emitted from the device is typically controlled through movable collimators. This type of system has several severe limitations; the dose delivered to the area surrounding the target site receives as much or more radiation as the target itself. The limiting factor in treating tumors in many instances is the radiobiological effect, e.g., tissue damage, which may be delivered to the surrounding healthy tissue. In many cases, radiation therapy will be more effective if higher doses of radiation can be directed to the target site without subjecting the surrounding area to toxic amounts of radiation. Current practice typically incorporates laser positioning systems to determine patient location prior to treatment. This positioning is confirmed and recorded by placing a tattoo on the patients skin. The accuracy of this procedure requires that a treatment "margin" be included to compensate for the following types of factors: a) mislocation of a patient; b) growth of the target during the treatment program (which may take up to six weeks); and c) physiological movement of the position of the target between treatments (several days can elapse between treatments). Also, in treatments to date patients are administered radiation in a static modality, and the patient is not moved during the administration of radiation during treatment.

Current technology for therapy systems requires that external shielding, typically 24–60 inches of reinforced concrete, be utilized to prevent generalized exposure to the scattered radiation present in the treatment room. The requirement for this shielding has restricted treatment rooms to locations in facilities which can support the resulting high floor weight loadings.

SUMMARY OF THE INVENTION

This invention features a stereotactically directable radiation therapy system (the system) for administering radioactivity to a patient. The system provides lower skin doses of radiation and improved targeting localization of the primary radiation dose to a patient. The system is designed to be fully integrated so as to provide a high degree of interface between the diagnostic, planning, and treatment phases. A radiation source beam unit which allows for increased radiation delivered to a tumor while decreasing the radiation received by surrounding tissue is provided. A radiation beam catcher which is lightweight and absorbs at least 80% and preferably at least 90% of the emitted radiation is also provided. Methods of performing radiation surgery and radiation therapy on a patient utilizing the apparatus of the present invention are also provided.

The system comprises: a) a CT Unit, or in an alternative embodiment an MRI Unit. Commercially available CT and MRI units, as would be known to those in the art are suitable. Further, any means allowing for the visualization of the interior and surface of a patients body (a patient 3-D mapping means) which encodes the information derived from the patient such that the information may be further utilized to control the administration of radiation by the system to the patient, as would be known in the art, is an acceptable component of the system. Any references to particular visualization means such as a CT scanner should be understood to be a preferred embodiment and not limiting of the scope of the invention. A CT scanner is preferably used to analyze hard tissue, for example, bone. An MRI unit is preferably used to analyze soft tissue, for example, the liver; b) a radiation source beam assembly (RSBA); the RSBA comprises a rotatable radiation source support means, in preferred embodiment a C-arm gantry, a radiation source beam unit (RSBU) affixed to the rotatable source means, a radiation shielding means, preferably a Tungsten collimator. The CT or MRI unit is affixed opposite the radiation source beam unit, d) a treatment table which has four degrees of freedom of movement, and e) a command and control center ("CCC"); the CCC comprises a central processing unit ("CPU"), the CPU may be any commercially available, for example, a pentium® chip. Any processing means which can manipulate the information received from a patient visualization means, for example, a CT unit, so as to control the administration of radiation to a patient by the system is suitable. The CCC includes treatment software which is commercially available, as would be known to those in the art, or alternatively specially modified software may be utilized. The CCC also comprises a control panel which allows one to, for example, position the patient on the treatment table and to preset treatment exposure times. The exposure time is controlled by an FDA approved timer or similar means as is known in the art. The CCC also comprises means for displaying information, for example, regarding the positioning of the treatment table and the elapsed time of treatment. A cathode ray tube or other display means and a mouse may also be included as part of the CCC. In an alternative embodiment the system further comprises a pedestal controller or similar in-treatment-room control means located in the treatment room. The pedestal controller is used to move the treatment table from within the treatment room.

The CT unit is located opposite of the RSBU, thereby providing for the ability to perform the necessary target localization procedure on the patient without any need for the patient to be removed from the table. The treatment software program processes the CT data, provides target localization data and allows a radiation treatment therapist to outline a target's margins "on-screen". The software provides dose planning, and defines treatment parameters.

The system incorporates multiple individual radiation sources, in a preferred embodiment seven Cobalt 60 sources. The focus of the individual beams emanating from the radiation sources intersects the target at a specific point relative to the central source position, preferably about 56 cm and initially contacts a patient a point relative to the central source position, preferably about 40 cm. A source holder assembly is secured in position and securely affixes the radiation sources in position to eliminate any focusing errors of the source beams. A rotating collimator positions the desired beam profile for the source beam position. The collimator movement preferably is accomplished within 1.5 seconds. The resulting sphere of radiation at the intersection of the beams is defined as the "treatment zone". This treatment zone encompasses spheres of radiation of varying diameters. In a preferred embodiment these diameters are 6.0, 14.0, 18.0 and 30.0 millimeters. By incorporating multiple intersecting radiation beams the system delivers a more intense radiation treatment to a defined target, while minimizing the radiation received by adjacent healthy tissue.

The system incorporates a "radiation beam catcher" which captures greater than 80% and preferably greater than 90% of the primary and scatter or penumbral radiation from the radioactive source material.

The "treatment table" is an integral part of the system. It can be controlled either by a joystick or directly by the treatment program software. Commercially available multimodality and 3-D planning and targeting software is suitable for this purpose. The joystick may be controlled by a DC stepper motor.

In another embodiment, the automatic positioning of the treatment table will also provide for "conformal therapy."

By "conformal therapy" is meant the process wherein a target which is larger than the treatment zone of the radiation sphere will be sequentially positioned until the entire target has received the designated dose of radiation imparted by the radiation sphere. The treatment table is preprogrammed to initialize the X, Y and Z coordinate positions so that the absolute table position relative to the radiation sphere is known to a predetermined accuracy, preferably of ±0.1 mm. The positioning of the table is verified through two modalities, a position transducer, and a shaft encoder, similar position verification means may be utilized. Both units verify position to a predetermined accuracy, preferably of ±0.1 mm and must agree, within set parameters at all times for the treatment table and RSBA to operate. A movable head frame may be included as necessary to allow for radiosurgical procedures on, for example, brain tumors. By "radiosurgery" or "radiosurgical" is meant the application of radiation to a patient in a single treatment session. In contrast, "radiotherapy" is the administration of radiation to a patient in more than one treatment session.

Other and further objects, features and advantages will be apparent from the following description of the presently preferred embodiments of the invention.

DETAILED DESCRIPTION OF THE INVENTION

The drawings will first briefly be described.

Figure 1:
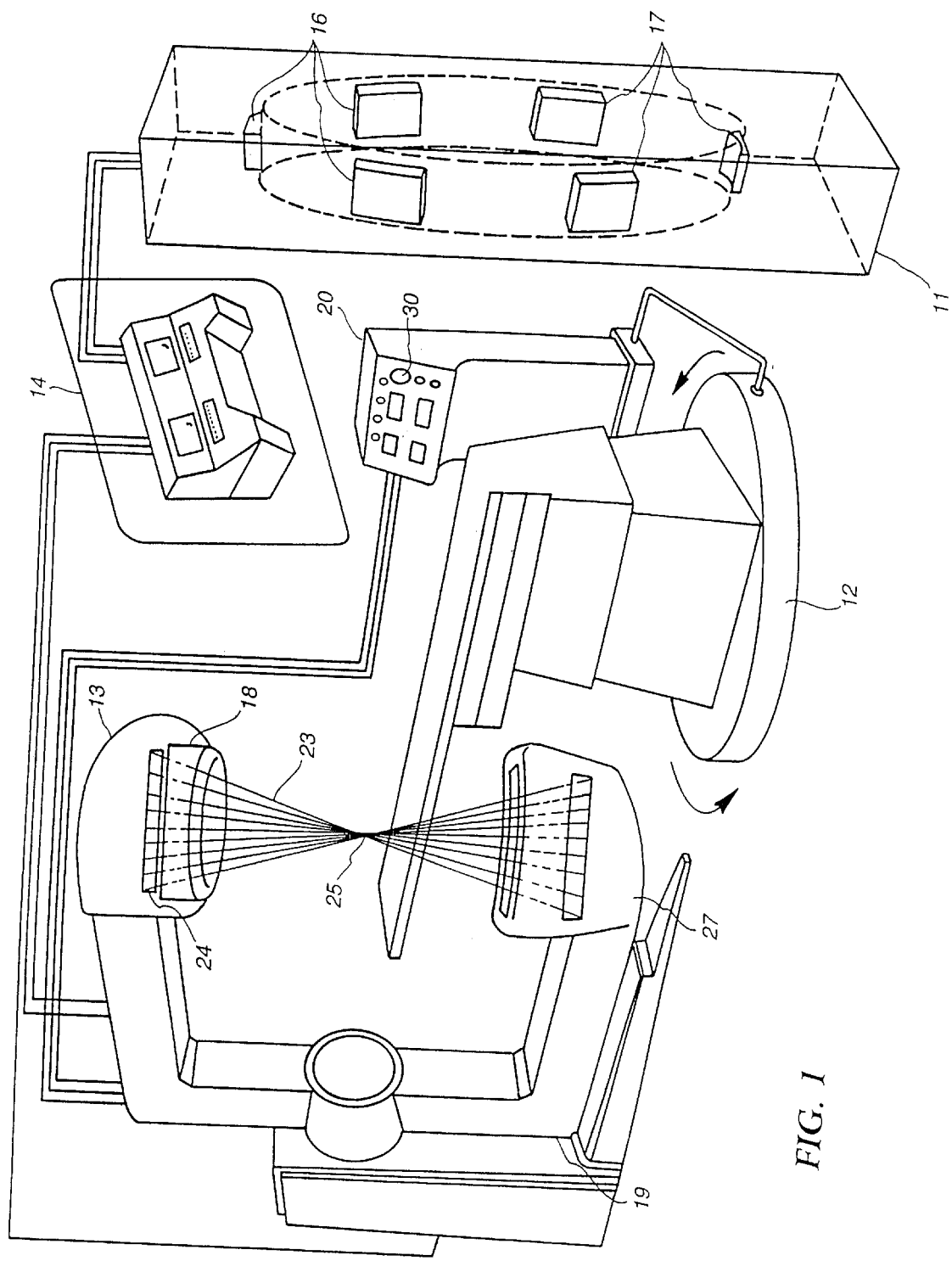
FIG. 1 illustrates the components of the system.

Turning in detail to the drawings, FIG. 1 illustrates a CT, MRI unit or other patient visualization means 11 containing X-ray tubes or comparable means 16 and detectors 17. A treatment table, rotatable about a central axis 12. A radiation source beam assembly (RSBA) 13 containing a radiation source beam assembly (RSBU) 24, which contains radioactive sources which emit beams of radiation 23, intersecting to form a treatment zone 25, and which are captured within a radiation beam catcher 27. The RSBA 13 includes a collimator 18. The RSBU 24 and radiation beam catcher 27 are supported on a rotatable source support means such as a C-arm gantry 19. A command and control center (CCC) 14 receives information from the CT or MRI 11 processes this information and in turn controls the RSBA 13. In an alternative embodiment, a pedestal controller 20 may be used to position the RSBA 13 from within the treatment room. The pedestal controller 30 contains an emergency off switch 20.

Figure 2:
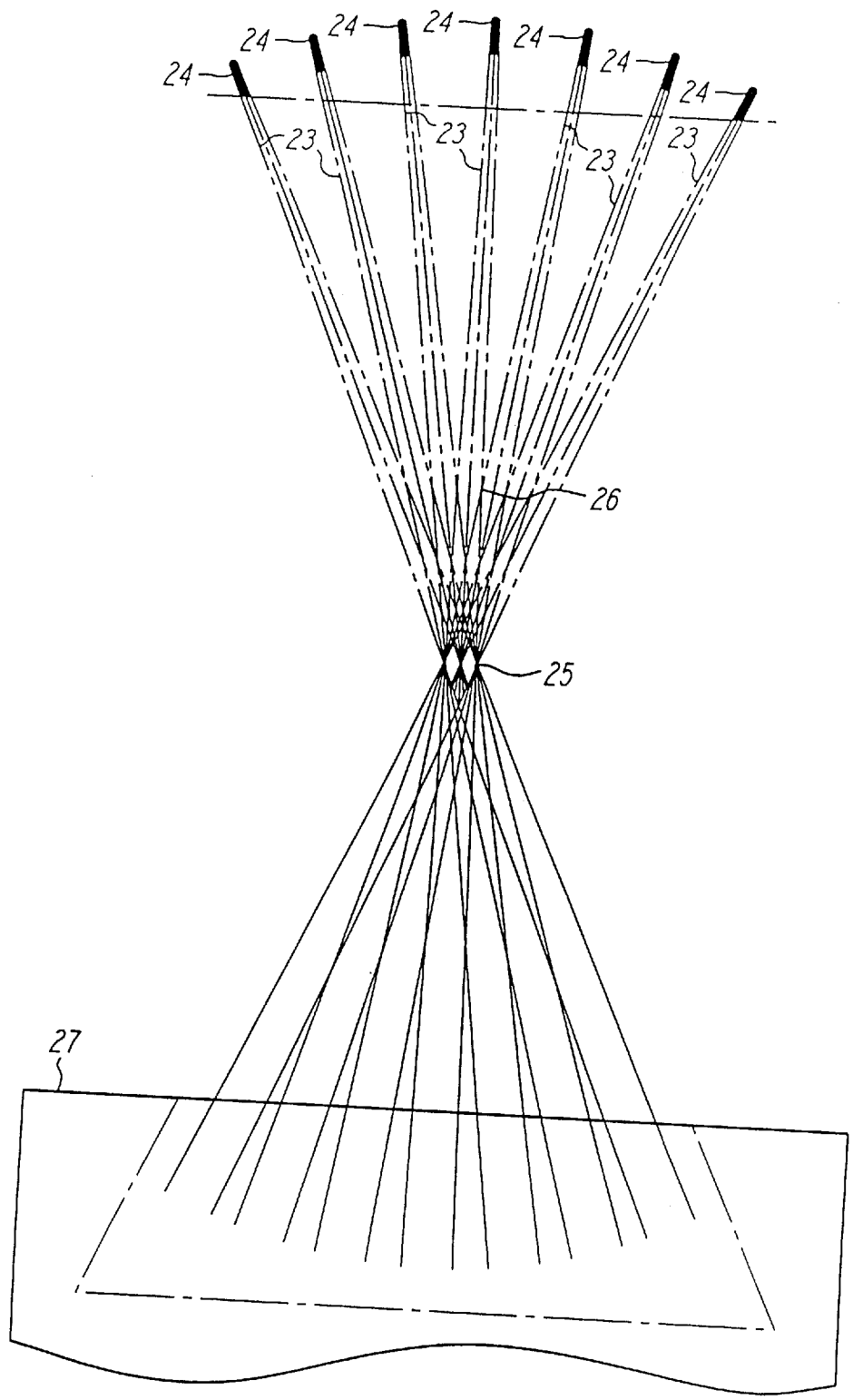
FIG. 2 illustrates the interaction pattern of the radiation source beams in the preferred embodiment with seven collimated beams of radiant energy.

FIG. 2 illustrates in more detail the geometry of the radiation source beams 23 as emitted from the RSBU 24. The treatment zone 25 is the focal point of the source beams. The configuration of the radiation source beams at position 26, the initial point of intersection of the source beams, illustrate the decreased radiation dose received by healthy tissue not in the target zone.

Figure 3:
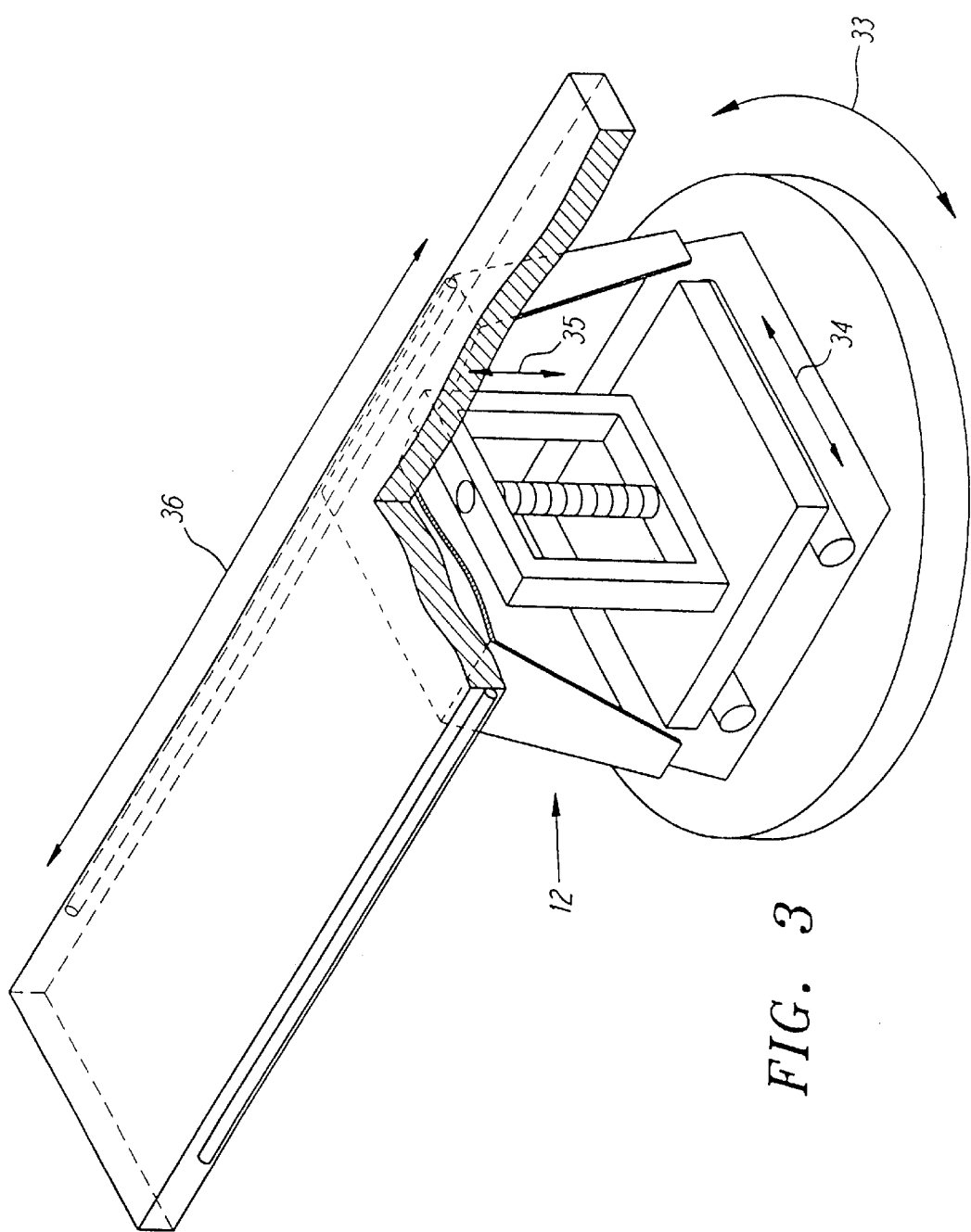
FIG. 3 illustrates the treatment table, depicting the four axis of movement.

FIG. 3 illustrates in more detail the axis of motion of the treatment table 12. Horizontal motion is provided for 36. Vertical motion is provided for 35. Lateral motion is provided for 34 and rotational motion is provided for 33.

Figure 4:
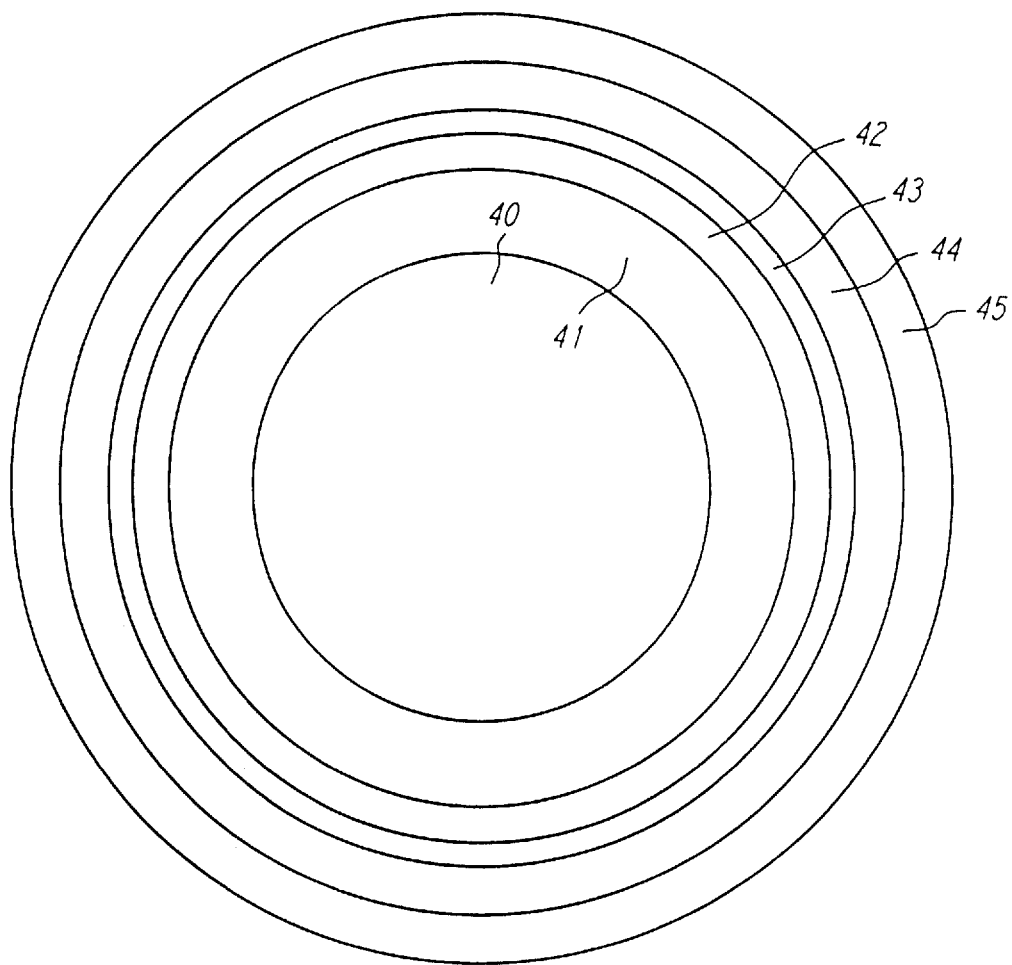
FIG. 4 illustrates the isodose profile of the radiant energy beams at 6.0 mm collimation. Other collimation will emulate this geometry.

FIG. 4 illustrates the isodose profile at 6.0 mm of collimation. The 100% isodose region is depicted by 40. The 90% isodose region is depicted by 41. The 80% isodose region is depicted by 42. The 70% isodose region is depicted by 43. The 60% isodose region is depicted by 44. The 50% isodose region is depicted by 45.

Figure 5:
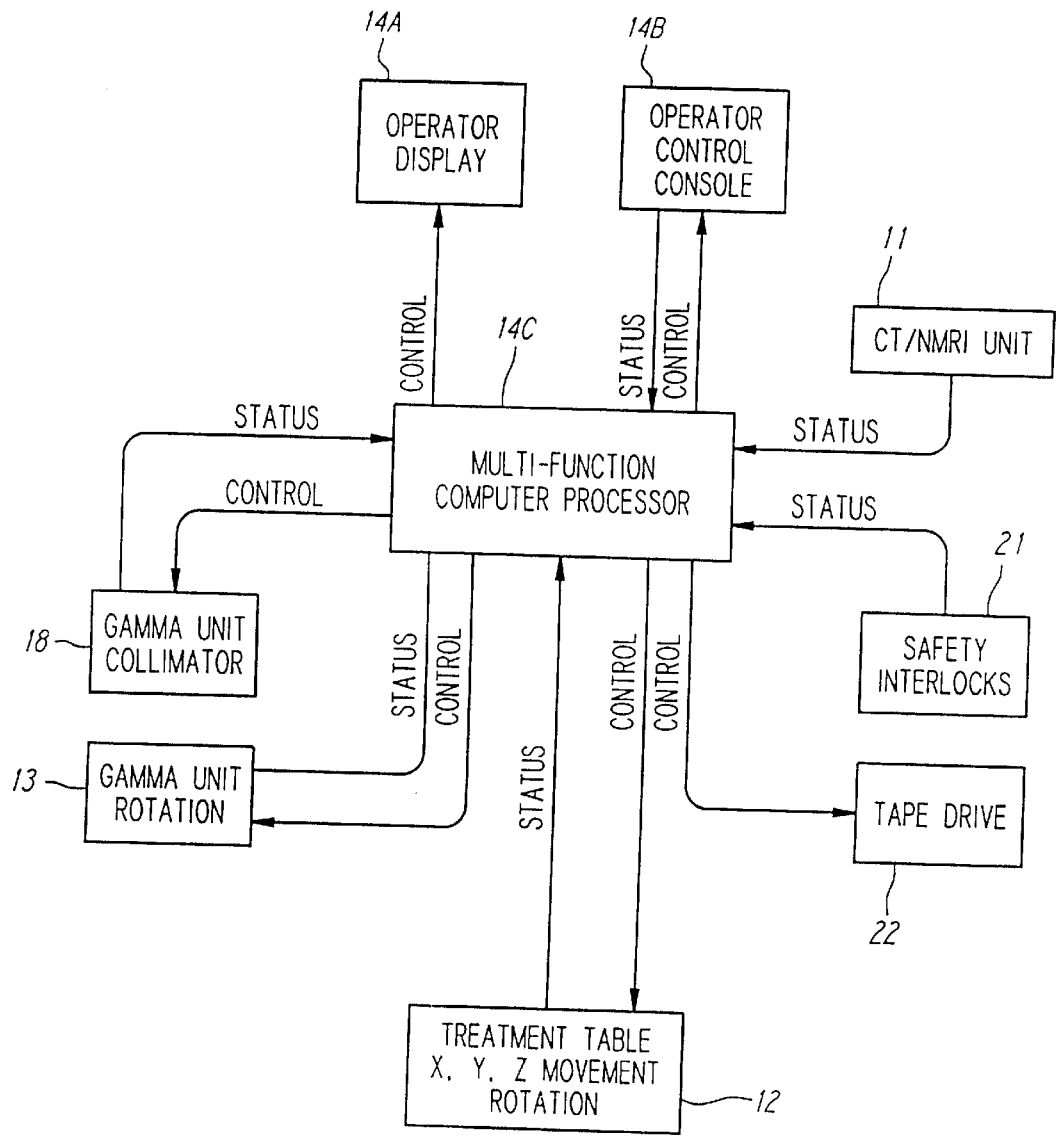
FIG. 5 is a block diagram illustrating the flow of information and commands between different components and subcomponents of the system.

FIG. 5 illustrates in block diagram form the interactions between the components and subcomponents of the system. The subcomponents of the command and control center 14, 14A, 14B and 14C are connected such that the multifunction computer processor or CPU 14C controls the output of the operator display 14A. The operator control console 14B is controlled by the CPU 14C and send information to the CPU 14C. The CT or MRI unit sends information to the CPU 14C. The CPU 14C also receives information from safety interlocks 21 which are provided to avoid inadvertent radiation exposure. The CPU 14C controls a tape drive or similar information recording and retrieval means 22. The treatment table 12 is controlled by the CPU 14C and provides information to the CPU 14C. The RSBA 13 is also controlled by the CPU 14C and provides information to the CPU 14C. The radiation source beam unit collimator 18 is also controlled by the CPU 14C and provides information to the CPU 14C.

Figure 6:
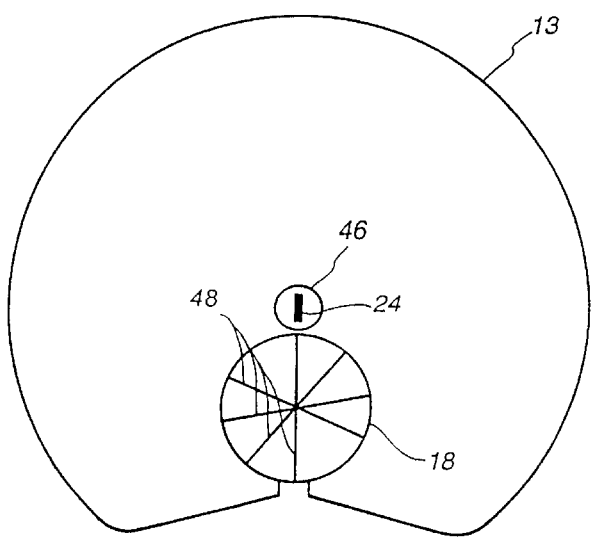
FIG. 6 illustrates the cross-sectional front view of the RSBA.

FIG. 6 illustrates the cross-sectional front view of the RSBA 13. This cross-sectional view details the radioactive sources 24 which are loaded into a source holder 46. This source holder holds the radioactive sources 24 in a fixed position throughout all motions of the RSBA 13. The rotational collimator 18 is depicted with the four distinct beamports 48 for each radioactive source 24. In this embodiment all four beamports are integrated into the single rotational collimator 18.

Figure 7:
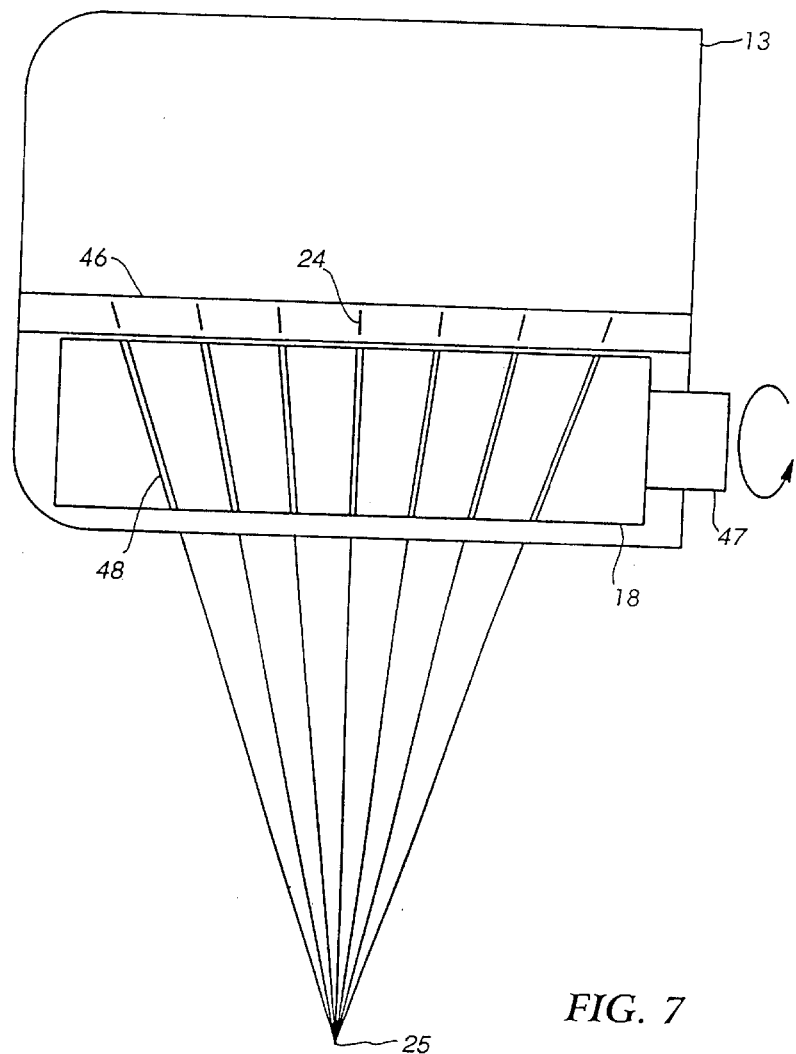
FIG. 7 illustrates the cross-sectional side view of the RSBA.

FIG. 7 illustrates the cross-sectional side view of the RSBA 13. This cross-sectional view depicts the radioactive sources 24 which are affixed in the source holder 46. The rotational collimator 18 is shown with one of the four beamports 48 in the "ON" position. A rotator 47 rotates the rotational collimator 18 into alignment with the radioactive sources 24 to deliver the beams of radiation to the treatment zone 25. The size of the treatment zone 25 can be varied by the positioning of the rotational collimator 18.

The system operates in the following manner. A patient is placed on the treatment table. The treatment table is rotated so as to enter the CT or MRI unit. In the case of MRI, the treatment table must be constructed of materials compatible with an MRI. Most generally, this excludes the use of metal for that part of the treatment table which actually enters the MRI unit. Suitable materials include honeycomb reinforced plastics or composite materials such as plastic or graphite composites. In a preferred embodiment, the dose reduction/ scatter coefficient for table attenuation is less than 1.5% as compare to the industry standard of 8%. This feature more readily allows for treatments utilizing a 360 degree rotation of the RSBA and reduces scatter radiation contribution from the table to the room by 20%. In another preferred embodiment, a heated table top may be included for patient comfort. Imaging data generated from the CT or MRI unit is encoded and transferred into the central processing unit (CPU) of the CCC. The CT or MRI unit is controlled from the control panel provided with the CT or MRI unit. The treatment table provides four axes of movement: Vertical, Lateral, Horizontal, and Rotational. In preferred embodiments the range of motion of travel is as follows: X Travel—of preferably 1000 mm; Y Travel of preferably 150 mm each side 300 mm total; Z Travel of preferably 300 mm and Rotation of preferably 360 degrees. These movements can be controlled by a technician through the pedestal controller located adjacent to the treatment table. The patient is positioned on the treatment table with the target site area located so as to be accessible to the RSBU. The patient is secured to prevent shifting of the target area during the procedure. Patients undergoing stereotactic radiosurgical procedures of the head may be secured in a head frame and the frame will be affixed to a mating component on the treatment table. The patient may be anesthetized to the degree necessary to prevent movement during the treatment. Once the patient is positioned and secured on the treatment table, a technician will actuate a "home" switch on the pedestal controller. In a preferred embodiment, this will automatically: a. rotate the table 180 degrees to position it in the CT or MRI unit; b. center the table laterally in the CT or MRI unit opening; c. vertically adjust the table so that the treatment table top is within a range of 0–200 mm, preferably 100 mm, below X and Y centerline coordinates of the CT or MRI unit. Once this is accomplished, the technician actuates a "CT center" switch on the pedestal controller or the CCC. This moves the treatment table to a preprogrammed position within the CT or MRI unit. The technician will then leave the treatment room. The treatment table is embedded with X (horizontal) and Z (lateral) reference markers which are visible on the CT or MRI display, for example, for the CT a metal and for the MRI, preferably aluminum is used as reference marker material. A one slice CT or MRI image is taken and the data is compared to the "calibration reference data" (CRD) for this position to verify X, Y, and Z positioning. Once this position is confirmed, the technician then moves the table to a second preprogrammed position at the end of the table travel. The table has identical reference markers embedded at this position. A second one slice CT or MRI image is taken and compared to the CRD. The CRD comprises a CT slice of each of two reference positions taken upon initial manufacture of the system. Agreement between the two scans and the CRD will validate and verify the four axes of movement of the treatment table. The technician can then move the treatment table to the desired target site and scan the patient until adequate data is obtained to determine target X, Y, and Z coordinates. When this data accumulation task is complete, the technician actuates the "home" switch on the control panel. This brings the table back to the position identified above, as set forth in steps a–c. Multiple lasers, preferably three, may be mounted on the RSBA. The treatment table has three reference points which will confirm location of the table relative to the RSBA to a predetermined accuracy, preferably of ±0.5 mm. The technician may then enter the room and confirm the treatment table location. The technician will then move the treatment table to the initial X, Y, and Z coordinates, determined by the treatment planning software to define the tumor site. The technician may utilize the pedestal controller for this task. Digital readouts on the pedestal controller confirm treatment table location at the three points to a predetermined accuracy, preferably of ±0.1 mm. Preferably, the pedestal controller display will also display the degree of rotation of the treatment table through its 360 degree range of motion. The pedestal controller for safety purposes cannot operate the CT or RSBA or RSBU. The technician may then proceed to the CCC or alternatively, the functions performed at the pedestal controller may have all been performed at the CCC.

The treatment plan, which has been determined in the planning stage by a physician and radiation treatment specialists, utilizing commercially available planning software, will detail the treatment parameters concerning: 1. specific beam collimation, and 2. type of therapy: a. static therapy; b. rotational therapy; c. skip/scan therapy; or d. conformal therapy. Each of these treatment parameters provides for specific treatment options, and are defined as follows: 1. Beam collimation may be varied based on the machining of the taper of the collimators as is known in the art. In a preferred embodiment, four different collimation settings resulting in 6.0, 14.0, 18.0, or 30.0 mm radiation spheres are provided. Therapeutic irradiation of a target of any size may be accomplished through the manipulation of the following variables: Movement of the treatment table through any of its three axes and rotation, and 360 degree rotation of the radiation source, and selection of the size of the treatment zone. A complete record of each individual treatment is part of the patient file which is available from computer memory.

The different methods of treatment are defined as follows: Static therapy—the treatment table remains motionless and the RSBA does not rotate while the patient is exposed to the radiation beams; rotational therapy—the treatment table remains motionless and the RSBA rotates up to 360 degrees while the patient is exposed to the radiation beams; skip/ scan therapy—the treatment table remains motionless during each irradiation sequence of the RSBU. The RSBA rotates up to 360 degrees with the collimation being changed or turned off during a portion of the rotation. This portion is determined during the planning stage by the physician and other radiation therapy specialists, utilizing commercially available planning software. After completion of one irradiation sequence, the treatment table can then position an additional target, which may be a separate tumor or another location of the same tumor, in the treatment zone, and the RSBA performs another sequence; conformal therapy —during this procedure all parameters are variable while the patient is exposed to the radiation beams. The control of the treatment table during conformal therapy may be carried out by CAD/CAM programs which convert the CT or MRI data to machine language allowing automatic targeting of the RSBA. Conformal therapy allows for the treatment of irregularly shaped tumors with a minimum of radiation delivered to surrounding healthy tissue. Utilizing CAD/CAM programs, as are commercially available, the collimation and hence the size of the treatment zone can be varied, preferably within 0.5 seconds, thereby allowing for accurate following of the contours of a tumor and not surrounding healthy tissue. Further, by moving the patient and not the radiation beams, better access to tumors and better ability to treat irregularly shaped tumors is provided. The CPU on the control console preprograms all movements prior to initiation of treatment. Utilizing this treatment modality, any size or shape target can be irradiated to therapeutic level with minimal radiobiological effects to surrounding healthy tissue. The rotational capability of the treatment table may be locked out during all treatments to prevent inadvertent treatment table RSBA collision. The RSBA comprises a rotatable support means, preferably a C-arm type gantry which rotates clockwise or counter-clockwise in a 360 degree range of movement. The depth of the C-arm to the point of maximal intersection of the radiation beams, e.g., the treatment zone should allow for easy accessibility of the treatment zone to regions of the patient when the treatment table is moved. Preferably a 1.0 Meter depth of the c-arm gantry arms to beam centerline will provide for good patient accessibility. An RSBU of the RSBA incorporates multiple radiation sources, preferably seven radiation sources, preferably each 800–1200 curies, most preferably each 1,000 curie Cobalt 60 Radioactive Special Form sources, as defined in 49 CFR 173.398, fixed in position. The sources are arranged in a non-radial arrangement, that is they are not arranged as if on the surface of a sphere or a curved portion of a sphere. Preferably, they are arrayed in a two-dimensional pattern, most preferably in a linear arrangement. A collimator, preferably tungsten, for example HD 17 tungsten, incorporating multiple, preferably four each collimator openings as designed to deliver a range of diameter of radiation beams, preferably 6.0, 14.0, 18.0 and 30 mm beams of radiation from each source is provided. These beams intersect at a point a particular distance from the central source (Isocenter), in one embodiment of this invention this distance is 56 cm and the point of initial intersection of the beams is 40 cm. This intersection is defined as the treatment zone. The dose rate provided thereby is 400 roentgen at the treatment zone. The particular point of intersection, and hence the treatment zone may vary but could be determined by one of ordinary skill in the art taking into account the following factors: The desired dose rate at the treatment zone; the minimum clear distance required between the patient and the RSBU; the amount of shielding needed, typically based on Federal regulations setting forth permissible radiation exposures; the desire to locate the radiation sources as close as possible to the treatment zone; the strength of each source to be used; the number of sources used and the distance between the sources. By varying these parameters, as would be known to one of ordinary skill in the art, the point of intersection of the beams may be varied. Factors such as cost of sources and the weight of a resulting system may also be considered in designing the system. Alternatively, the treatment zone could remain the same while a variation of the other parameters would allow for differences in, for example, the number of radiation sources used and their spacing. In a preferred embodiment the above-listed parameters are arranged so that, at the maximal collimation, e.g., the largest treatment zone diameter, the treatment zone will coincide with a deep tumor, e.g., approximately six inches below the skin and the surface of the patient will coincide with a point at which the radiation beams initially intersect. (See FIG. 2). This arrangement of the beams provides for decreased radiation exposure to healthy tissue. For example, in a typical Cobalt 60 device a source may be located 80–100 cm from the tumor, utilizing 7000 curies in the sources, 150–200 Roentgen/minute is delivered to the tumor and at the patient's surface is exposed to the full 7000 curies of radioactivity. In contrast, this invention provides for, in a specific embodiment, a separation of 56 cm between the tumor and source, utilizing 7000 curies in the sources, 400 Roentgen/minute is delivered, however only 1000 curies are delivered to the skin, although because of the closer source distance the nominal decrease in dosage with the system of the present invention is 25% and not one seventh of that provided by a typical cobalt 60 source unit.

Any position on the outer surface of the sphere of radiation that is produced, in the treatment zone, should not vary in position in any direction by more than 1.0 mm, and preferably by more than 0.5 mm, as the RSBA rotates through its 360 degree movement. An absolute encoder or similar device as is known in the art, will sense RSBA rotation to an accuracy of ±0.1–0.5 degrees, preferably ±0.25 degrees. All four collimated beams for each of the multiple radiation sources will focus the radiation about the same point in space. In one embodiment, beam trimmers may be provided at about 30 cm from source isocenter to more precisely focus the radiation and create a sharper beam profile. The beam trimmers may be removable. The beam trimmers mount to the face of the RSBA, specifically the RSBU. Preferably the beam trimmer is of tungsten and contains machined holes to direct the radiation beam as is known in the art. Beam trimmers are generally only used for treatment of tumors located in the head and not in the body. All RSBU and RSBA controls are located on the control console. The RSBU and RSBA will not operate until all room interlocks are closed. These interlocks may consist of a safety/lockout switch located on the RSBA, a keyed enable circuit located on the treatment room wall, and a door interlock switch which senses the position of the access door (open/closed) to the treatment room. Mushroom style or other suitable "panic" switches may be located on some or all treatment room walls. The keyed enable switch can also be used as the system active switch on the control console.

Secondary "scatter" radiation resulting from the primary beam impinging a surface is dealt with in a unique way. Typical "beam stoppers" are immense slabs of lead/steel, which are large enough to deflect the largest collimation from a standard teletherapy unit which is approximately 35 cm×35 cm at 80 cm from the source centerline. The convex surface of these beam stoppers attempts to deflect the scatter radiation back to the source head.

The radiation beam catcher of the present invention actually captures the primary radiation beams from the source head and focuses the scattered radiation within the radiation beam catcher cavity. The radiation beam catcher comprises side walls and a bottom which define a cavity of the beam catcher. The size of the cavity is a multiple of the widest radiation source beam width, e.g., in a preferred embodiment the collimation at 30 cm multiplied by the longest beam length plus 5–20 cm. In a preferred embodiment, the size of the cavity is 1.75 times the widest beam width in the lateral dimension multiplied by the longest beam length plus 10 cm. The depth of the cavity is preferably at least 15 cm deep. The walls of the radiation beam catcher match the radiation beam profile angle of the largest collimated beam of the RSBU. The base of the cavity resembles an inverted pyramid. The angle of declination of the walls of the inverted pyramid may vary from 20–45 degrees, preferably it is 25 degrees. The lowest point of the pyramid is located at the center of the opening of the cavity. The inverted pyramidal surface contains multiple pyramids of a defined height, preferably 1.3 cm. These pyramids are irregularly spaced on the surface of the inverted pyramidal base, the number and spacing of such pyramids may be determined so as to maximize the amount of radiation captured within the beam catcher, as could easily be determined by one of ordinary skill in the art. These baffles within the radiation beam catcher capture the primary beam, and focus the scatter within the radiation beam catcher. In a preferred embodiment, the radiation beam catcher further includes at the top of the walls defining the cavity, tungsten elements to project any scatter emitted from the radiation beam catcher back to the RSBU. These tungsten elements may be rectangular. Preferably, they are one half inch in width and one inch in height. The radiation beam catcher thus reduces the necessary treatment room shielding and allows placement of the imaging unit, CT or MRI in close proximity to the RSBA.

The CCC performs. multiple functions: a. It will process 2-D imaging data into a 3-D imaging format for therapy planning use; b. It will control the imaging unit, treatment table, and RSBA and RSBU. This control can be either manual or automatic; c. It will record all localization and treatment data. These records can be used to determine target growth, shrinkage, or movement during radiotherapy, or for patient follow-up after radiosurgical procedures; d. An "emergency off" switch which automatically shuts down the RSBU within a specified time period, preferably 2.0 seconds; e. The CCC may provide on-screen treatment simulation to allow the physician to review a treatment and determine all dose levels delivered to both the target and adjacent tissue. This process can be repeated and varied until the physician has optimized the treatment. This simulation is accomplished by integration of 3-D CT or MRI data with treatment planning software which is commercially available; f. Actual treatment time is controlled by an FDA-approved electronic timer fitted to the control panel. In a preferred embodiment, this timer cannot be overridden and is accurate to ±1 second, most preferably 0.6 seconds.

All patents and publications mentioned in this specification are indicative of the levels of those skilled in the art to which the invention pertains. All patents and publications are herein incorporated by reference to the same extent as if each individual publication was specifically and individually indicated to be incorporated by reference. One skilled in the art will readily appreciate that the present invention is well adapted to carry out the objects and obtain the ends and advantages mentioned, as well as those inherent therein. The methods, procedures, treatments, and apparatus described herein are presently representative of preferred embodiments, are exemplary and are not intended as limitations on the scope of the invention. Changes therein and other uses will occur to those skilled in the art which are encompassed within the spirit of the invention as defined by the scope of the claims.

What is claimed is:

1. A method for administering radiation to a patient comprising:
    (a) executing treatment planning software on the central processing unit of a command and control center in order to determine a set of X,Y and Z radiation therapy target coordinates;
    (b) providing three-dimensional visualization information to said central processing unit for use in determining said set of X,Y and Z radiation therapy target coordinates;
    (c) providing treatment table position status to said central processing unit;
    (d) performing both three-dimensional visualization and radiation therapy treatment without removing the patient from said treatment table; and
    (e) catching the radiation from said radiation therapy in a radiation beam catcher.

2. The method for administering radiation to a patient of claim 1 wherein the step of providing three-dimensional visualization information to said central processing unit for use in determining said set of X,Y and Z radiation therapy target coordinates provides information from a computerized tomographic scanner.

3. The method for administering radiation to a patient of claim 1 wherein the step of providing three-dimensional visualization information to said central processing unit for use in determining said set of X,Y and Z radiation therapy target coordinates provides information from a magnetic resonance imaging system.

4. The method for administering radiation to a patient of claim 1 further comprising determining the position of said treatment table relative to said radiation source beam assembly based on said set of X,Y, and Z radiation therapy coordinates.

5. The method for administering radiation to a patient of claim 1 further comprising preprogramnming the treatment table to initialize the X,Y, and Z Coordinate positions So that the absolute table position relative to the radiation sphere is known to a predetermined accuracy.

6. The method for administering radiation to a patient of claim 1 further comprising the step of controlling the position of a radiation source beam assembly with a pedestal controller.

7. The method for administering radiation to a patient of a claim 1 further comprising the step of controlling the position of said treatment table automatically with a central processing unit.

8. The method for administering radiation to a patient of a claim 1 further comprising the step of controlling the position of said treatment table with a pedestal controller.

9. The method for administering radiation to a patient of claim 1 further comprising the step of executing CAD/CAM software such that control of said treatment table during conformal therapy may be automatically carried out by said CAD/CAM software.

10. The method for administering radiation to a patient of claim 1 further comprising the step of moving the treatment table from its three-dimensional visualization position to its radiation therapy treatment position by electronic means.

11. The method for administering radiation to a patient of claim 10 wherein said step of moving the treatment table from its three-dimensional visualization position to its radiation therapy position by electronic means comprises moving the treatment table by operating a pedestal controller.

12. The method for administering radiation to a patient of claim 1 further comprising the step of controlling the position of the treatment table by CAD/CAM programs said step further comprising converting said three-dimensional visualization information to machine language and positioning said table to permit automatic targeting of the treatment tissue.

* * * * *